United States Patent [19]

Yamaji et al.

[11] 4,401,808
[45] Aug. 30, 1983

[54] ADENOSINE CYCLIC 3',5'-PHOSPHATE TRIESTERS AND THE ACID ADDITION SALTS THEREOF, AND PROCESS FOR PRODUCTION THEREOF

[75] Inventors: Nobuyuki Yamaji; Motohiko Kato, both of Noda, Japan

[73] Assignee: Kikkoman Corporation, Chiba, Japan

[21] Appl. No.: 317,282

[22] Filed: Nov. 2, 1981

Related U.S. Application Data

[63] Continuation-in-part of Ser. No. 177,490, Aug. 12, 1979, abandoned.

[30] Foreign Application Priority Data

Aug. 13, 1979 [JP] Japan .............................. 54-102282

[51] Int. Cl.$^3$ ...................... C07H 19/20; C07H 19/00
[52] U.S. Cl. ......................................... 536/27; 536/28; 536/29
[58] Field of Search .............................. 536/27, 28, 29

[56] References Cited

PUBLICATIONS

Engels, J. and Schlaeger, E., J. Med. Chem., vol.207, pp. 907–911, 1977.
Gohil, R., et al., Nuclic Acid Research, vol.1, pp. 1691–1701, 1974.
Korth, M. and Engels, J., Archieves of Pharmacology, vol. 310, pp. 103–111, 1979.
Nagyvary, J., et al., Biochem. Biophys. Res. Comm., vol. 55, pp. 1072–1077, 1973.

Colton, F., et al., Proc. Nat. Acad. Sci. vol. 72, pp. 1335–1339, 1975.
Chemistry of Organic compounds, Ed. by Carl R. Noller, pp. 321–322, 1965, W. B. Saunders Company, Philadelphia.

*Primary Examiner*—Blondel Hazel
*Attorney, Agent, or Firm*—Sherman & Shalloway

[57] ABSTRACT

Triesters of adenosine cyclic 3',5'-phosphoric acid having cardiotonic, diuretic and anti-tumor activities represented by the following formula

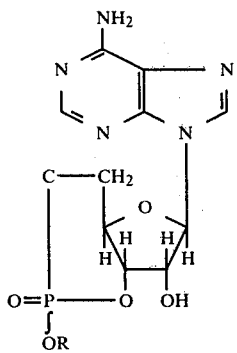

wherein R represents a linear or branched
alkyl group having 5 to 15 carbon atoms, and the acid addition salts thereof; and a process for production thereof.

3 Claims, No Drawings

ADENOSINE CYCLIC 3',5'-PHOSPHATE TRIESTERS AND THE ACID ADDITION SALTS THEREOF, AND PROCESS FOR PRODUCTION THEREOF

This application is a continuation-in-part application of U.S. patent application Ser. No. 177490 filed on Aug. 12, 1979, now abandoned.

This invention relates to adenosine cyclic 3',5'-phosphate triesters and the acid addition salts thereof which are not described in the prior art literature, and to an improved process for producing adenosine cyclic 3',5'-phosphate triesters and the acid addition salts thereof including the aforesaid novel compounds in higher yields using cheaper and more readily available reagents by an easier and simpler operation than in conventional processes.

Adenosine cyclic 3',5'-phosphoric acid (to be abbreviated "cAMP") of the following formula

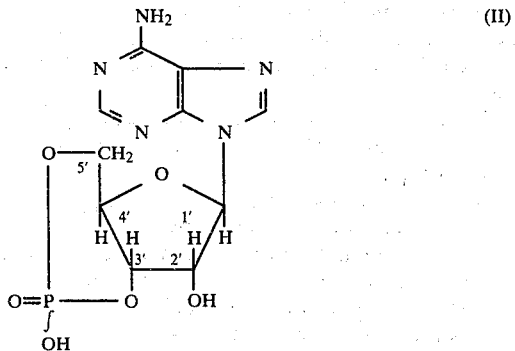

exists in the tissues of almost all kinds of mammals. It is known to be synthesized within the cells and to control some of the biological and metabolic activities of tissues. It has gradually been elucidated therefore that some diseases caused by disordered metabolism and internal secretion are due to the insufficient concentration of cAMP in the cells. Thus, a rational therapy of diseases of this type is to increase the concentration of cAMP in the cells by direct administration of cAMP. This, however, has the defect that cAMP has an inferior ability to penetrate cellular membranes and is susceptible to enzymatic degradation and its activity is not selective among tissues.

In an attempt to remove such a defect, investigations have been made on the synthesis and biological activities of cAMP derivatives.

For example, Nucleic Acids Research, Vol. 1, No. 12, 1974, pp 1691–1701 describes the synthesis of cAMP triesters and their physical-chemical properties under the title "Synthesis and properties of some cyclic AMP alkyl phosphotriesters". This article deals with the synthesis of methyl, ethyl, propyl, butyl and cetyl ($C_{16}$) triesters of cAMP. According to this article, the triesters are obtained only in low yields by using a tributyl ammonium salt of cAMP through complex operations, as shown in Referential Examples given hereinbelow. At pages 1699 to 1700, it is stated that the best yield of methyl-cAMP is 33%, the best yield of ethyl-cAMP is 45%, and the yield of propyl-cAMP is 22%. It is also stated that the initial yield of 65% for butyl-cAMP dropped to 20% after repeated chromatography on silica gel which was necessary to separate some 2'-O-mesyl derivative, and that the initial yield of cetyl-cAMP was as small as 5%.

Experiments of the present inventors tracing the work set out in the aforesaid article have shown that the yield of ethyl-cAMP is 14%, and butyl and heptyl cAMP do not form in detectable amounts (see Referential Example 1 given hereinbelow). It is presumed that according to the method of this prior art reference, the alcohol reagent used decreases in reactivity with a longer chain length of its alkyl group.

Journal of Medicinal Chemistry, Vol. 20, No. 7, 1977, pp. 907–190 gives an article entitled "Synthesis, Structure, and Reactivity of Adenosine Cyclic 3',5'-Phosphate Benzyl Triesters". This article reported that methyl-cAMP was obtained in a yield of 47% from cAMP and ethereal diazomethane from N-methyl-N-nitrosourea, ethyl-cAMP was obtained in a yield of 42% from cAMP and ethereal diazoethane from N-ethyl-N-nitrourea, benzyl-cAMP was obtained in a yield of 58% from cAMP and ethereal phenyldiazomethane from N-nitroso-N'-nitro-N-benzylguanidine, and by using the corresponding other diazo derivatives, o-nitrobenzyl-cAMP in a yield of 43%, p-nitrobenzyl-cAMP in a yield of 33% and p-methylbenzyl-cAMP in a yield of 25% were synthesized. The method described in this article also requires expensive reagents which are difficult to obtain, and the yields of the esters are not satisfactory.

Furthermore, Journal of Medicinal Chemistry, Vol. 16, No. 12, 1973, pp. 1319–1323 gives an article entitled "Synthesis and Enzymic Studies of 5-Aminoimidazole and N-1- and $N^6$-Substituted Adenine Ribonucleoside Cyclic 3',5'-Phosphates Prepared from Adenosine Cyclic 3',5'-Phosphate." The article describes the reaction of a cAMP salt with an alkyl halide at page 1320, right column, lines 15 to 14 from the bottom. It specifically discloses that the reaction of a DBU salt (DBU=1,5-diazabicyclo[5.4.0]-5-undecene salt) of cAMP with methyl iodide in dimethyl sulfoxide gives 1-methyladenosine cyclic 3',5'-phosphate with the bonding of a methyl group to N at the 1-position of the purine ring of cAMP.

A similar reaction is disclosed in Japanese Laid-Open Patent Publication No. 92094/1974 (laid open on Sept. 3, 1974). This patent document states that the reaction of cAMP or its alkali salt with an alkyl halide results in the introduction of the alkyl group of the alkyl halide into N at the 1-position of the purine ring of cAMP.

The present inventors worked extensively in order to develop a process for producing adenosine cyclic 3',5'-phosphate triesters in high yields by an easy and simple operation using inexpensive and easily available raw materials and reagents, which process is free from the disadvantages and defects of conventional processes exemplified hereinabove.

This work has led to the discovery that adenosine cyclic 3',5'-phosphate triesters of the following formula

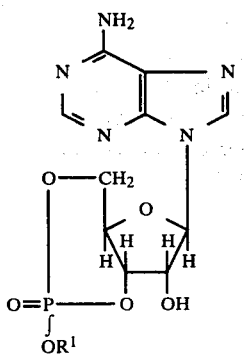

wherein R¹ represents a linear or branched alkyl group having 1 to 20 carbon atoms, or the acid addition salts thereof can be obtained by reacting cAMP of formula (II) or its salt with an alkyl halide of the following formula $$R^1-X \quad \text{(III)}$$

wherein R¹ is as defined above and X represents a halogen atom,
in the presence of a base in the absence or presence of a solvent, and optionally converting the resulting product into its acid addition salt.

As disclosed in the above-cited J.M. Chem., Vol. 16, No. 12 and Japanese Laid-Open Patent Publication No. 92094/74, the reaction between cAMP or its salt and an alkyl halide results in the selective introduction of an alkyl group into N at the 1-position of the purine ring of cAMP. In contrast, it is quite unexpected from the disclosures of the above-cited literature references that the reaction of cAMP or its salt with an alkyl halide in the presence of a base in accordance with the process of this invention selectively gives adenosine cyclic 3',5'-phosphate triester. Thus, the many disadvantages and defects of the prior art in the production of the above-mentioned triester can be overcome and removed by the process of this invention, and adenosine cyclic 3',5'-phosphate triester can be produced in high yields by an easy and simple operation using inexpensive and easily available raw materials and reagents.

The compounds of formula (I)' include adenosine cyclic 3',5'-phosphate triesters of the following formula

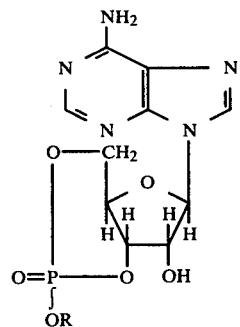

wherein R represents a linear or branched alkyl group having 5 to 15 carbon atoms,
and the acid addition salts thereof which are difficult to synthesize by conventional processes and are not described in the prior art literature. Such novel compounds have been found to be easily synthesizable in high yields by reacting cAMP of formula (II) or its salt with a compound of the formula R—X (III)' (wherein R is as defined above, and X is a halogen atom) in the presence of a base in the absence or presence of a solvent, and optionally converting the resulting product into its acid addition salt.

It has been found that the compounds of formula (I)' including the novel compounds of formula (I) have good ability to penetrate cellular membranes, show high biological activities which have selectivity among various target tissues, and are stable to a degrading enzyme, cAMP phosphodiesterase. In particular they have cardiotonic, diuretic and anti-tumor activities. For example, the novel compounds of formula (I) are useful in controlling malignant tumors or cancer, such as leukemia.

It is an object of this invention therefore to provide adenosine cyclic 3',5'-phosphate triesters of formula (I) and the acid addition salts thereof which are not described in the prior art literature.

Another object of this invention is to provide a novel and improved process for producing the compounds of formula (I)' including the novel compounds of formula (I).

The above and other objects and advantages of this invention will become more apparent from the following description.

According to this invention, the compounds of formula (I)' and their acid addition salts including the novel compounds of formula (I) can be produced easily in high yields by reacting cAMP of formula (II) or its salt with an alkyl halide of formula (III) in the presence of a base in the absence or presence of a solvent, and optionally converting the resulting product into its acid addition salt.

The starting cAMP of formula (II) can be used either in free form or in salt form. Compounds which form a salt at the cyclic 3',5'-phosphate moiety can be used as the salt. From the viewpoint of solubility in solvents, the salt is preferably in the form of an organic ammonium salt. Examples of the organic ammonium salt are tri-lower alkyl ammonium salts such as triethylammonium salts and tributyl ammonium salts, and 4-morpholino-N,N'-dicyclohexylcarboxyamidine salt.

The halogen atom X in formula (II) and (III)' is preferably Cl, Br or I. Specific examples of the alkylating agent (III) or (III)' are methyl iodide, ethyl iodide, propyl bromide, isopropyl iodide, isopropyl bromide, butyl iodide, butyl bromide, butyl chloride, isobutyl iodide, pentyl bromide, isopentyl bromide, hexyl bromide, heptyl bromide, octyl bromide, nonyl bromide, decyl bromide, decyl chloride, undecyl bromide, dodecyl bromide, tridecyl bromide, tetradecyl bromide, pentadecyl bromide, hexadecyl bromide, heptadecyl bromide, octadecyl bromide, nonyldecyl bromide, and eicosyl bromide. The alkyl groups in the above alkylating agents include both linear and branched alkyl groups.

Both inorganic and organic bases can be used as the base which is present in the reaction system. Examples of the inorganic bases include alkali metal hydroxides, alkali metal carbonates, alkali metal bicarbonates, and inorganic amines. Specific examples are sodium hydroxide, potassium hydroxide, sodium carbonate, potassium carbonate, sodium hydrogen carbonate, potassium hydrogen carbonate, and ammonium hydroxide. Organic amines, preferably tertiary amines, can be cited as the organic bases. Specific examples of such organic amines are trialkylamines such as triethylamine and tributylamine, pyridine, picoline, and lutidine. These bases can be used either singly or in combination with each other.

Inert organic solvents capable of dissolving cAMP or its salts may be used as the reaction solvent. Alternatively, an excess of an organic base is used in the reaction to cause it to serve concurrently as a solvent, and in this embodiment, it is not particularly necessary to use an inert organic solvent. Those inert organic solvents which have a high degree of solubility for cAMP or its salts are preferably used. It is also preferred to use those solvents which will increase the reactivity of the alkyl halide of formula (III). Specific examples of the inert organic solvent include amides such as dimethyl formamide and dimethyl acetamide, nitriles such as acetonitrile and benzonitrile, alkyl sulfoxides such as dimethyl sulfoxide, alcohols such as methanol, ethanol, propanol and butanol, and aromatic hydrocarbons such as benzene and toluene. These solvents can be used either singly or in combination with each other. Preferably, these solvents are used in an anhydrous or substantially anhydrous condition.

The reaction can be performed by contacting cAMP of formula (II) or its salt with the alkyl halide of formula (III) in the presence of the above-exemplified base in the absence or presence of the above-exemplified solvent.

The amount of the alkyl halide (III) is not particularly restricted, and for example, may be about 1 to about 10 moles, preferably about 3 moles to about 10 moles, per mole of cAMP or its salt. The amount of the base used may also be selected suitably, and it may be used in an excessive amount to cause it to serve concurrently as a solvent. Preferably, the amount of the base is that which is sufficient to maintain the reaction system substantially neutral to alkaline from the beginning or the early stage to the end of the reaction. The base may be added all at once to the reaction system at the beginning or in the early stage of the reaction, or it may be added portionwise continuously or at intervals.

The reaction can be carried out at a temperature ranging, for example, from room temperature to about 180° C., preferably about 70° to about 120° C. The reaction time can be selected as desired, and may be varied depending upon the types of the alkyl halide and the solvent, the reaction temperature, etc. For example, the reaction time is about 10 minutes to about 5 hours.

After the reaction, the final desired product can be isolated and purified by conventional methods, for example by column chromatography on activated carbon, ion exchange resins, alumina, silica gel, etc., extraction with organic solvents such as chloroform and ethyl acetate, precipitation with organic solvents, and crystallization by pH adjustment in suitable combinations. For example, after the reaction, the reaction mixture is concentrated under reduced pressure to remove the solvent, and chloroform in an amount sufficient for the final product to be adsorbed to alumina is added to the residue. The mixture is then passed through an alumina column at room temperature to cause adsorption of the final product to the alumina. Then, the column is washed with chloroform, and eluted with a mixture of chloroform and methanol to separate the cAMP triester. The eluate containing the desired cAMP triester is concentrated, or is crystallized by addition of a solvent to obtain the final product.

Depending upon the purifying conditions, the compound of this invention can be obtained in the form of either a free base or its acid addition salt. The acid addition salt can be represented by the following formula

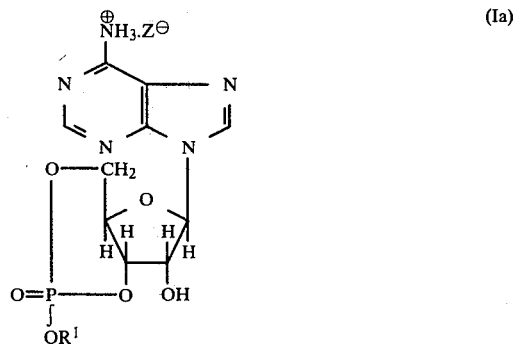

wherein $R^1$ is as defined with regard to formula (I)', and $Z^\ominus$ represents an anion.

The acid addition salt can also be formed by converting the compound of formula (I)' into its acid addition salt by means known per se. For example, the conversion to the acid addition salt can be effected by adding an aqueous or alcohol solution of an acid to the free base of formula (I)' to adjust the pH of the system to not more than about 3. The resulting acid addition salt of formula (Ia) can be isolated as a solid by evaporating the reaction mixture to dryness, or by adding to the reaction mixture a non-solvent for the acid addition salt of formula (Ia) or a solvent capable of only sparingly dissolving the acid addition salt (Ia), such as alcohol, acetone, dioxane, ether or hexane to precipitate it. Compounds of formula (I)' in which $R^1$ represents an alkyl group having not more than 14 carbon atoms are preferably converted into their acid addition salts (Ia) because such acid addition salts have especially increased solubility and are suitable for end uses.

The acid addition salts are preferably addition salts of pharmaceutically acceptable acids, both organic and inorganic. Use of inorganic acids such as hydrochloric acid, hydrobromic acid, sulfuric acid, nitric acid and phosphoric acid is preferred.

The following examples illustrate the present invention more specifically.

REFERENTIAL EXAMPLE 1

Synthesis of cAMP ethyl triester by a conventional method:

Well-dried cAMP tri-n-butylammonium salt (1.0 g) was dissolved in a mixture of 5 ml of pyridine and 0.9 ml of tri-n-butylamine. The solution was maintained at 0° C., and a solution of 0.73 g of p-toluenesulfonyl chloride in 2 ml of pyridine was added to the solution. The mixture was reacted for 2 minutes, and then 8 millimoles of anhydrous ethanol was added. The solution was allowed to stand at 5° C. for 30 minutes, and concentrated to one-third of its initial volume under reduced pressure. To the concentrate were added 1.2 ml of tri-n-butylamine and a solution of 1.09 g of p-toluenesulfonyl chloride in 5 ml of pyridine, and the mixture was reacted at 0° C. for 2 minutes. The reaction mixture was again reacted using 12 millimoles of ethanol under conditions such that the reaction temperature was raised from 0° to 20° C. during 30 minutes. Ethanol (20 ml)

was added to the reaction mixture, and the reaction was stopped. The reaction mixture was concentrated to a gum which was extracted twice with 20 ml of toluene-1% triethylamine. The remaining gum as an extraction residue was mixed with 10 g of silica gel using toluene-ethanol 1:1. The mixture was dried, and placed on the upper portion of a silica gel column (50×2 cm). The column was first washed with 100 ml of toluene and then eluted with 200 ml of toluene-20% ethanol and 800 ml of toluene-30% ethanol to obtain 20 ml-fractions. Those fractions which contained the final desired product were concentrated. The concentrate was passed through a column (45×2 cm) of Amberlite CG-400 (Cl form), and the column was eluted with 50% pyridine aqueous solution. Fractions which contained the final desired product were concentrated, and passed through a column (2×10 cm) of Sephadex G-25 for desalting. The column was eluted with water. Fractions containing the final desired product were concentrated to afford 98.4 mg (yield 14%) of ethyl triester of cAMP as crystals.

REFERENTIAL EXAMPLE 2

Synthesis of n-butyl triester of cAMP by a conventional method:

Anhydrous n-butanol was added to cAMP activated in the same way as in Referential Example 1. The solution was reacted by operating in the same way as in Referential Example 1. After the reaction, the reaction mixture was analyzed by paper chromatography. No spot corresponding to the final product could be determined.

REFERENTIAL EXAMPLE 3

Synthesis of n-heptyl triester of cAMP by a conventional method:

Anhydrous n-heptyl alcohol was added to cAMP activated in the same way as in Referential Example 1. The solution was reacted by operating in the same way as in Referential Example 1. After the reaction, the reaction mixture was analyzed by paper chromatography. No spot corresponding to the final product could be determined.

REFERENTIAL EXAMPLE 4

Pharmacological test on leukemia:

$CDF_1$ mice were used as test animals. Test compounds indicated below were administered to one group consisting of 6 mice. Ten $CDF_1$ mice were used for control.

Test compound

Control compound:
n-butyl triester of adenosine cyclic 3',5'-phosphoric acid (cAMP-$C_4$ triester)

Compound of this invention:
n-pentyl triester of adenosine cyclic 3',5'-phosphoric acid (cAMP-$C_5$ triester)
n-decyl triester of adenosine cyclic 3',5'-phosphonic acid (cAMP-$C_{10}$ triester)

In each $CDF_1$ mouse were intraperitoneally inoculated $5\times10^4$ leukemia cells L-1210. After the lapse of 24 hours from the inoculation, a solution of each test compound in dimethyl sulfoxide was administered intraperitoneally once a day at a dose of 30 mg/kg over a period of 5 days. The results were evaluated through Increased Life Span (ILS) as shown in Table A.

TABLE A

| Test compound | ILS (%) |
|---|---|
| cAMP-$C_4$ triester (control) | 0 |
| cAMP-$C_5$ triester (this invention) | 5.6 |
| cAMP-$C_{10}$ triester (this invention) | 18.1 |

EXAMPLE 1

One gram of cAMP was dissolved in a mixture of 5 ml of water, 5 ml of ethanol and 1.5 ml of tri-n-butylamine. The solution was concentrated under reduced pressure at 30° to 40° C., and dried under reduced pressure using phosphorus pentoxide to afford tri-n-butylammonium salt of cAMP. The resulting cAMP salt was dissolved in 50 ml of dehydrated dimethyl formamide, and 5 ml of tri-n-butylamine and 2 ml of ethyl iodide were added. The reaction was performed at 80° C. for 3 hours.

The reaction mixture was concentrated to about 7 ml under reduced pressure, and dissolved in a small amount of water. The pH of the solution was adjusted to 2 with 2 N hydrochloric acid. The solution was caused to be adsorbed to a column (1.4 cm in diameter and 20 cm in length) filled with activated carbon. The column was washed with 200 ml of water, and then eluted with a mixture of ethanol, water and 28% aqueous ammonia (volumn ratio 10:10:1). The eluates were concentrated to remove ethanol and ammonia, adjusted to pH 2 with 2 N hydrochloric acid, and adsorbed to a column (1.4 cm in diameter and 20 cm in length) of Dowex 1 (acetic acid form). The column was eluted with water. Fractions containing the final desired product (showing an ultraviolet absorption at 260 nm) were collected, and concentrated to afford 164 mg of ethyl triester of cAMP as crystals.

Melting point: 195°–197° C.

Rf value in filter paper chromatography: 0.66 (developing solvent; 0.5 M ammonium acetate-ethanol=2:5).

Ultraviolet absorption spectrum:
$\lambda_{max}^{0.1\ N\text{-HCl}}$ 257.0 nm
$\lambda_{max}^{0.1\ N\text{-NaOH}}$ 260.0 nm One hundred (100) milligrams of the cAmP ethyl triester obtained as above was suspended in 2 ml of water, and 0.6 ml of 1 N hydrochloric acid was added. The solution was concentrated to dryness under reduced pressure to afford 115 mg of cAMP ethyl triester hydrochloride having a melting point of 157° to 160° C. (decomp.). The physicochemical properties of the resulting product coincided with those of the cAMP ethyl triester obtained above.

By similarly treating the cAMP ethyl triester with hydrobromic acid, sulfuric acid, nitric acid and phosphoric acid respectively instead of hydrochloric acid, the hydrobromide, sulfate, nitrate and phosphate were respectively obtained.

EXAMPLE 2

The same reaction as in Example 1 was carried out using 3 ml of n-butyl iodide instead of 2 ml of ethyl iodide. The reaction mixture was worked up in the same way as in Example 1. Fractions containing the final desired product were concentrated to 0.5 ml. When 3 ml of ethanol and 50 ml of ether were successively added to the concentrate, n-butyl triester of cAMP precipitated in an amount of 118 mg.

Melting point: 117°–119° C.

Rf value in filter paper chromatography: 0.67 (the same developing solvent as in Example 1).

Ultraviolet absorption spectrum:
$\lambda_{max}^{0.1\ N\text{-}HCl}$ 257.0 nm
$\lambda_{max}^{0.1\ N\text{-}NaOH}$ 260.0 nm By operating in the same way as in Example 1, inorganic acid salts of the above product were obtained.

EXAMPLE 3

The same reaction as in Example 1 was performed using 3 ml of n-pentyl iodide instead of 2 ml of ethyl iodide. The reaction mixture was worked up in the same way as in Example 2 to afford 97 mg of n-pentyl triester of cAMP.

Melting point: 109°–111° C.

Rf value in filter paper chromatography: 0.72 (the same developing solvent as used in Example 1)

Ultraviolet absorption spectrum:
$\lambda_{max}^{0.1}$ N-HCl 257.0 nm
$\lambda_{max}^{0.1}$ N-NaOH 260.0 nm By operating in the same way as in Example 1, inorganic acid salts of the above product were obtained.

EXAMPLE 4

One gram of tri-n-butylammonium salt of cAMP was dissolved in 100 ml of dimethyl formamide, and 5 ml of tri-n-butylamine and 4 ml of n-decyl bromide were added. The reaction was performed at 100° C. for 1 hour. After the reaction, the reaction mixture was concentrated under reduced pressure, and 100 ml of chloroform was added to the concentrate. The mixture was adsorbed to a column (2.2 cm in diameter and 21 cm in length) of 60 g of alumina. The column was washed with 150 ml of chloroform and eluted with 800 ml of methanol-chloroform (volume ratio 1:99). The eluates were concentrated, and n-hexane was added to precipitate n-decyl triester of cAMP in an amount of 505 mg.

Melting point: 70°–72° C.

Rf value in filter paper chromatography: 0.81 (the same developing solvent as in Example 1)

Ultraviolet absorption spectrum:
$\lambda_{max}^{0.1}$ N-HCl 257.0 nm
$\lambda_{max}^{0.1}$ N-NaOH 260.0 nm By operating in the same way as in Example 1, inorganic acid salts of the above product were obtained.

EXAMPLE 5

The same reaction as in Example 4 was carried out using 5 ml of n-tetradecyl bromide instead of n-decyl bromide. The reaction mixture was worked up in the same way as in Example 4 to afford 203 mg of n-tetradecyl triester of cAMP.

Melting point: 74°–76° C.

Rf value in filter paper chromatography: 0.82 (the same developing solvent as used in Example 1)

Ultraviolet absorption spectrum:
$\lambda_{max}^{0.1\ N\text{-}HCl}$ 257.0 nm
$\lambda_{max}^{0.1\ N\text{-}NaOH}$ 260.0 nm By operating in the same way as in Example 1, inorganic acid salts of the above product were obtained.

EXAMPLE 6

One gram of tri-n-butylammonium salt of cAMP was dissolved in 100 ml of dimethyl formamide, and 5 ml of tri-n-butylamine and 6 ml of n-hexadecyl bromide were added. The reaction was performed at 120° C. for 30 minutes. The reaction mixture was worked up in the same way as in Example 4 to afford 238 mg of n-hexadecyl triester of cAMP.

Melting point: 76°–78° C.

Rf value in filter paper chromatography: 0.83 (the same developing solvent as used in Example 1)

Ultraviolet absorption spectrum:
$\lambda_{max}^{0.1}$ N-HCl 257.0 nm
$\lambda_{max}^{0.1}$ N-NaOH 260.0 nm By operating in the same way as in Example 1, inorganic acid salts of the above product were obtained.

EXAMPLE 7

The same reaction as in Example 4 was carried out at 120° C. for 1 hour using 7 ml of stearyl bromide instead of 4 ml of n-decyl bromide. There was obtained 228 mg of stearyl triester of cAMP.

Melting point: 78°–80° C.

Rf value in filter paper chromatography: 0.84 (the same developing solvent as used in Example 1)

Ultraviolet absorption spectrum:
$\lambda_{max}^{0.1}$ N-HCL 257.0 nm
$\lambda_{max}^{0.1}$ N-NaOH 260.0 nm By operating in the same way as in Example 1, inorganic acid salts of the above product were obtained.

EXAMPLE 8

One gram of tri-n-butylammonium salt of cAMP was dissolved in 50 ml of dimethyl formamide, and 5 ml of tri-n-butylamine and 3 ml of isobutyl bromide were added. The reaction was performed at 120° C. for 3 hours. After the reaction, the reaction mixture was concentrated under reduced pressure, and 100 ml of chloroform was added to the concentrate. The mixture was adsorbed to a column (2.2 cm in diameter and 14 cm in length) of 40 g of alumina. The column was successively washed with 150 ml of chloroform and 150 ml of methanol-chloroform (volume ratio 2:98), and then eluted successively with 200 ml of each of a 5:95 (by volume) mixture of methanol and chloroform and a 10:90 (by volume) mixture of methanol and chloroform. The eluates were concentrated, and then n-hexane was added to precipitate isobutyl triester of cAMP in an amount of 130 mg.

Rf value in filter paper chromatography: 0.67 (the same developing solvent as used in Example 1)

Ultraviolet absorption spectrum:
$\lambda_{max}^{0.1}$ N-HCl 257.0 nm
$\lambda_{max}^{0.1}$ N-NaOH 260.0 nm Infrared absorption spectrum:
$\nu$2950, 1645, 1600, 1280, 1000 cm$^{-1}$ By operating in the same way as in Example 1, inorganic acid salts of the above product were obtained.

EXAMPLE 9

One gram of free cAMP was dissolved under heat in a mixture of 100 ml of dimethyl formamide and 10 ml of tri-n-butylamine, and 4 ml of n-decyl bromide was added. The reaction and work-up were performed in the same way as in Example 4 to afford 570 mg of n-decyl triester of cAMP. The physico-chemical properties of the product coincided with those of the compound obtained in Example 4.

EXAMPLE 10

The procedure of Example 4 was performed except that 4 ml of each of the alkylating agents indicated in Table 1 was used instead of n-decyl bromide, and the reaction was carried out at 120° C. The melting points of the triesters of cAMP obtained are shown in Table 1.

TABLE 1

| Alkylating agent | Triester of cAMP | Melting point (°C.) |
| --- | --- | --- |
| n-Hexyl bromide | cAMPC$_6$H$_{13}$ | 78–82 |
| n-Heptyl bromide | cAMPC$_7$H$_{15}$ | 76–81 |
| n-Octyl bromide | cAMPC$_8$H$_{17}$ | 76–82 |
| n-Nonyl bromide | cAMPC$_9$H$_{19}$ | 83–89 |
| n-Undecyl bromide | cAMPC$_{11}$H$_{23}$ | 67–75 |
| n-Dodecyl bromide | cAMPC$_{12}$H$_{25}$ | 74–80 |
| n-Tridecyl bromide | cAMPC$_{13}$H$_{27}$ | 85–90 |
| n-Pentadecyl bromide | cAMPC$_{15}$H$_{31}$ | 78–84 |

By operating in the same way as in Example 1, inorganic acid salts of the above products were obtained.

What we claim is:

1. A process for producing triesters of adenosine cyclic 3',5'-phosphoric acid of the following formula

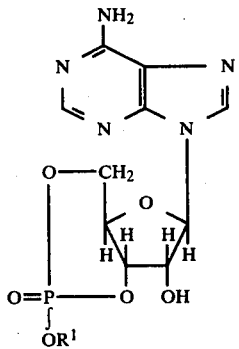

(I)' wherein R$^1$ represents a linear or branched alkyl group having 1 to 20 carbon atoms, or the acid addition salts thereof, which comprises reacting an adenosine cyclic 3',5'-phosphoric acid of the following formula

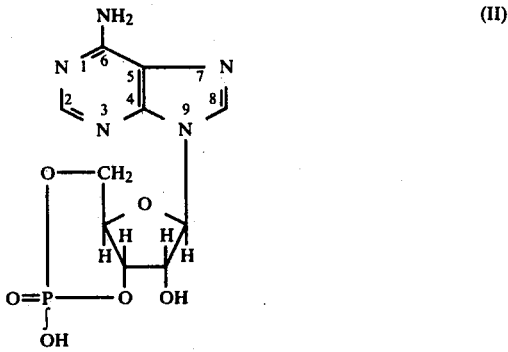

(II)

or its salt with an alkyl halide of the following formula

R$^1$—X (III)

wherein R$^1$ is as defined above, and X represents a halogen atom,
in the presence of a base in the absence or presence of a solvent.

2. The process of claim 1 wherein said reaction is carried out at room temperature to about 180° C.

3. The process of claim 1 wherein said salt of the adenosine cyclic 3',5'-phosphoric acid of formula (II) is an organic ammonium salt of the phosphoric acid (II).

* * * * *